(12) United States Patent
Hauer et al.

(10) Patent No.: US 8,932,837 B2
(45) Date of Patent: Jan. 13, 2015

(54) AMIDASE AND USE THEREOF FOR PRODUCING 3-AMINOCARBOXYLIC ACID ESTERS

(71) Applicant: BASF SE, Ludwigshafen (DE)

(72) Inventors: Bernhard Hauer, Fussgönheim (DE); Thomas Friedrich, Ratingen (DE); Rainer Stürmer, Ródersheim-Gronau (DE); Nina Schneider, Offenburg (DE); Susanne Sabrowski, Kleinblittersdorf (DE); Wolf-Rüdiger Krahnert, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/942,184

(22) Filed: Jul. 15, 2013

(65) Prior Publication Data
US 2013/0337512 A1    Dec. 19, 2013

Related U.S. Application Data

(62) Division of application No. 13/497,985, filed as application No. PCT/EP2010/064098 on Sep. 24, 2010, now abandoned.

(30) Foreign Application Priority Data

Sep. 25, 2009    (EP) .................... 09171414

(51) Int. Cl.
| | |
|---|---|
| C12P 13/00 | (2006.01) |
| C12N 9/80 | (2006.01) |
| C12N 9/16 | (2006.01) |
| C12P 13/04 | (2006.01) |
| C12P 41/00 | (2006.01) |

(52) U.S. Cl.
CPC .............. C12P 13/001 (2013.01); C12N 9/80 (2013.01); C12P 13/04 (2013.01); C12P 41/007 (2013.01)
USPC .......................... 435/128; 435/196; 435/197

(58) Field of Classification Search
CPC ........ C12P 13/001; C12P 41/007; C12N 9/80
USPC ......................... 435/128, 196, 197
See application file for complete search history.

(56) References Cited

U.S. PATENT DOCUMENTS

| | | |
|---|---|---|
| 4,652,657 A | 3/1987 | Broger et al. |
| 5,177,220 A | 1/1993 | Schafer et al. |
| 2009/0299089 A1 | 12/2009 | Jaekel et al. |

FOREIGN PATENT DOCUMENTS

| | | |
|---|---|---|
| EP | 0 158 875 A2 | 10/1985 |
| EP | 0437690 A2 | 7/1991 |
| EP | 1882740 A1 | 1/2008 |
| JP | 2008182986 A | 8/2008 |
| WO | WO-97/41214 A1 | 11/1997 |
| WO | WO-2008/003761 A1 | 1/2008 |

OTHER PUBLICATIONS

International Preliminary Report on Patentability for PCT/EP2010/064098, issued Apr. 3, 2012.
"SubName: Full=Putative amidase; EC=3.5.1.-;", Uniprot Database, Accession No. C1A2X4, May 26, 2009.

*Primary Examiner* — Tekchand Saidha
*Assistant Examiner* — Md. Younus Meah
(74) *Attorney, Agent, or Firm* — Drinker Biddle & Reath LLP

(57) ABSTRACT

Process for producing optically active 3-aminocarboxylic acid ester compounds of general Formula I, and the ammonium salts thereof,

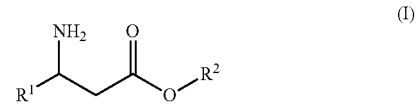

in which $R^1$ stands for alkyl, alkoxyalkyl, alkenyl, cycloalkyl, heterocycloalkyl, aryl, or hetaryl, and $R^2$ stands for alkyl, cycloalkyl or aryl, in which an enantiomeric mixture of a simply N-acylated 3-aminocarboxylic acid ester of general formula (I.b),

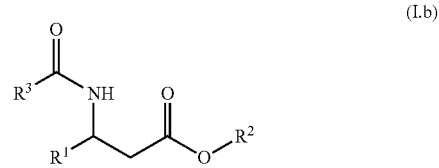

in which $R^1$ and $R^2$ have the meanings given above and $R^3$ stands for hydrogen, alkyl, cycloalkyl or aryl, is submitted to an enantioselective deacylation by adding a polypeptide according to claim 1.

6 Claims, 3 Drawing Sheets

Concentration of 3-acetylamino-3-phenyl-propionic acid ethyl ester

Formation of 3-amino-3-phenyl-propionic acid ethyl ester

Comparison of reaction with racemic or enantiomer-enriched substrate

Reaction of enriched S-AAPEE

SEQUENCE LISTING

<160> NUMBER OF SEQ ID NOS: 4

<210> SEQ ID NO 1
<211> LENGTH: 1419
<212> TYPE: DNA
<213> ORGANISM: Rhodococcus equi
<220> FEATURE:
<221> NAME/KEY: CDS
<222> LOCATION: (1)..(1419)

<400> SEQUENCE: 1

| | | |
|---|---|---|
| atg agt aca tcg gat ccg ggt tgg atg ccg gcg acc gag atg gcc gcc<br>Met Ser Thr Ser Asp Pro Gly Trp Met Pro Ala Thr Glu Met Ala Ala<br>1                       5                      10                    15 | 48 |
| cag gtc gcc tcg aag aga ttg tcg ccc aac gag atc gca gag gag atg<br>Gln Val Ala Ser Lys Arg Leu Ser Pro Asn Glu Ile Ala Glu Glu Met<br>                  20                    25                    30 | 96 |
| atc cgt cga gtc gag gag gtc aat ccc tcc gtc aac gcg atc gtg cac<br>Ile Arg Arg Val Glu Glu Val Asn Pro Ser Val Asn Ala Ile Val His<br>        35                    40                    45 | 144 |
| ttc gac gcc gag cag gtg cgc cgc gac gcc gcc gac ctg gca cgg gcg<br>Phe Asp Ala Glu Gln Val Arg Arg Asp Ala Ala Asp Leu Ala Arg Ala<br>50                      55                    60 | 192 |
| cag gag agc ggt gag acg ctc ggt ccg ctc cac ggc gtc ccg ttc acg<br>Gln Glu Ser Gly Glu Thr Leu Gly Pro Leu His Gly Val Pro Phe Thr<br>65                      70                    75                    80 | 240 |
| atc aag gac ctc acc gac gtc cgt ggc ctg ccg acc acg ttc ggc ctg<br>Ile Lys Asp Leu Thr Asp Val Arg Gly Leu Pro Thr Thr Phe Gly Leu<br>                  85                    90                    95 | 288 |
| aag ccc atg cgc gac aac atc gcc gaa cgc gac gcg gtg atc gtc acc<br>Lys Pro Met Arg Asp Asn Ile Ala Glu Arg Asp Ala Val Ile Val Thr<br>                      100                  105              110 | 336 |
| cgg ttg cgg cag gcc ggc ggc ctc tac ctc ggc aag acc aac acc ccg<br>Arg Leu Arg Gln Ala Gly Gly Leu Tyr Leu Gly Lys Thr Asn Thr Pro<br>115                    120                  125 | 384 |
| gag agc ggc tac tac ggc ggc acc gac aac cac ctg ttc ggc ccg acc<br>Glu Ser Gly Tyr Tyr Gly Gly Thr Asp Asn His Leu Phe Gly Pro Thr<br>130                    135                  140 | 432 |
| cac aat ccg tgg aag ccc ggc cac acc ccc ggc gga tcg agc ggt ggc<br>His Asn Pro Trp Lys Pro Gly His Thr Pro Gly Gly Ser Ser Gly Gly<br>145                    150                  155              160 | 480 |
| gcc gcc gcg gcc gtc gcc gcc ggt ctc ggt ccg ctc gcc gag ggc agc<br>Ala Ala Ala Ala Val Ala Ala Gly Leu Gly Pro Leu Ala Glu Gly Ser<br>                      165                  170              175 | 528 |
| gac ggc gcc ggg tcg gtc cgg atc ccg tcg gca ttg tgc ggc gtc gtc<br>Asp Gly Ala Gly Ser Val Arg Ile Pro Ser Ala Leu Cys Gly Val Val<br>180                    185                  190 | 576 |
| gga ctc aag ccc acg acc ggc gtg atc ccg cag acg atc ctg ccc ggc<br>Gly Leu Lys Pro Thr Thr Gly Val Ile Pro Gln Thr Ile Leu Pro Gly<br>195                    200                  205 | 624 |
| cgc tac aac aac tgg gcg tac cac ggt ccc atc acc cgc acc gtt gcc<br>Arg Tyr Asn Asn Trp Ala Tyr His Gly Pro Ile Thr Arg Thr Val Ala<br>210                    215                  220 | 672 |
| gac aac gcc ctg atg ctg gac gtt ctt gcc ggg ccg gat cat tcg gat<br>Asp Asn Ala Leu Met Leu Asp Val Leu Ala Gly Pro Asp His Ser Asp<br>225                    230                  235              240 | 720 |
| ccg ctg agc atc gaa cga gtc gag ggc tcg tac gtc gag gcg gcg cgg<br>Pro Leu Ser Ile Glu Arg Val Glu Gly Ser Tyr Val Glu Ala Ala Arg<br>                      245                  250              255 | 768 |
| ggt ggg atc gac ggg ctg cga gtc gcg tgg tcg ccg gac ctc ggt ctc<br>Gly Gly Ile Asp Gly Leu Arg Val Ala Trp Ser Pro Asp Leu Gly Leu<br>260                    265                  270 | 816 |
| ggc cac gtc gag ccc gac gtc gcc gcg gtc tgc gcc gag gcg gtc gcg<br>Gly His Val Glu Pro Asp Val Ala Ala Val Cys Ala Glu Ala Val Ala<br>275                    280                  285 | 864 |
| tgt ttc gag gag atg ggc gcc aag gtc gtc gag gcg acg ccg gac tgg<br>Cys Phe Glu Glu Met Gly Ala Lys Val Val Glu Ala Thr Pro Asp Trp<br>290                    295                  300 | 912 |

```
ggc gat ccg tcg gag gcg atg tgg cac ggc atc tgg gtg ccg ggc ttc      960
Gly Asp Pro Ser Glu Ala Met Trp His Gly Ile Trp Val Pro Gly Phe
305             310                 315                 320 gcc ggc gag cac gac atg ctc gac tgg gac gcg ctg cac ggc cag gtc     1008
Ala Gly Glu His Asp Met Leu Asp Trp Asp Ala Leu His Gly Gln Val
                325                 330                 335 gac gag aac ctg atc gaa ctg atc cac gag ggc cgg cga ctc acc ggc     1056
Asp Glu Asn Leu Ile Glu Leu Ile His Glu Gly Arg Arg Leu Thr Gly
            340                 345                 350 gtc gac tac ggc cgc gcc gac acg ttc cgc ggt ggc atg tgg gac acc     1104
Val Asp Tyr Gly Arg Ala Asp Thr Phe Arg Gly Gly Met Trp Asp Thr
        355                 360                 365 tgg acc gag ttc atg aac gac tac gac gtc ctg atc tcg ccg acg ctg     1152
Trp Thr Glu Phe Met Asn Asp Tyr Asp Val Leu Ile Ser Pro Thr Leu
    370                 375                 380 gcg tcc gcc acg ttc ccg ctc acc cag ttc gcg ccg gac tgg cta cag     1200
Ala Ser Ala Thr Phe Pro Leu Thr Gln Phe Ala Pro Asp Trp Leu Gln
385                 390                 395                 400 ggc aag tcg ctg cgc gag caa ctg ctc gac tgg ctg ctg acc tac ccg     1248
Gly Lys Ser Leu Arg Glu Gln Leu Leu Asp Trp Leu Leu Thr Tyr Pro
                405                 410                 415 tac aac atg ctg aac aac ccc gcg atc acg gtc ccc gca ggc ttc acc     1296
Tyr Asn Met Leu Asn Asn Pro Ala Ile Thr Val Pro Ala Gly Phe Thr
            420                 425                 430 ccg gac ggg cgc ccg gtc gga ctc cag atc gcg gcg cgc cat cgt cag     1344
Pro Asp Gly Arg Pro Val Gly Leu Gln Ile Ala Ala Arg His Arg Gln
        435                 440                 445 gac gcg ctc gtg ctg cgg gtc gcg gcg aac ctg gag cag gca cgg ccg     1392
Asp Ala Leu Val Leu Arg Val Ala Ala Asn Leu Glu Gln Ala Arg Pro
    450                 455                 460 tgg gcg gat cgt cga ccg gtg gcg tag                                 1419
Trp Ala Asp Arg Arg Pro Val Ala
465                 470

<210> SEQ ID NO 2
<211> LENGTH: 472
<212> TYPE: PRT
<213> ORGANISM: Rhodococcus equi

<400> SEQUENCE: 2

Met Ser Thr Ser Asp Pro Gly Trp Met Pro Ala Thr Glu Met Ala Ala
1               5                   10                  15

Gln Val Ala Ser Lys Arg Leu Ser Pro Asn Glu Ile Ala Glu Glu Met
            20                  25                  30

Ile Arg Arg Val Glu Glu Val Asn Pro Ser Val Asn Ala Ile Val His
        35                  40                  45

Phe Asp Ala Glu Gln Val Arg Arg Asp Ala Ala Asp Leu Ala Arg Ala
    50                  55                  60

Gln Glu Ser Gly Glu Thr Leu Gly Pro Leu His Gly Val Pro Phe Thr
65                  70                  75                  80

Ile Lys Asp Leu Thr Asp Val Arg Gly Leu Pro Thr Thr Phe Gly Leu
                85                  90                  95

Lys Pro Met Arg Asp Asn Ile Ala Glu Arg Asp Ala Val Ile Val Thr
            100                 105                 110

Arg Leu Arg Gln Ala Gly Gly Leu Tyr Leu Gly Lys Thr Asn Thr Pro
        115                 120                 125

Glu Ser Gly Tyr Tyr Gly Gly Thr Asp Asn His Leu Phe Gly Pro Thr
    130                 135                 140
```

```
His Asn Pro Trp Lys Pro Gly His Thr Pro Gly Ser Ser Gly Gly
145                 150                 155                 160

Ala Ala Ala Ala Val Ala Ala Gly Leu Gly Pro Leu Ala Glu Gly Ser
                165                 170                 175

Asp Gly Ala Gly Ser Val Arg Ile Pro Ser Ala Leu Cys Gly Val Val
            180                 185                 190

Gly Leu Lys Pro Thr Thr Gly Val Ile Pro Gln Thr Ile Leu Pro Gly
        195                 200                 205

Arg Tyr Asn Asn Trp Ala Tyr His Gly Pro Ile Thr Arg Thr Val Ala
    210                 215                 220

Asp Asn Ala Leu Met Leu Asp Val Leu Ala Gly Pro Asp His Ser Asp
225                 230                 235                 240

Pro Leu Ser Ile Glu Arg Val Glu Gly Ser Tyr Val Glu Ala Ala Arg
                245                 250                 255

Gly Gly Ile Asp Gly Leu Arg Val Ala Trp Ser Pro Asp Leu Gly Leu
            260                 265                 270

Gly His Val Glu Pro Asp Val Ala Ala Val Cys Ala Glu Ala Val Ala
        275                 280                 285

Cys Phe Glu Glu Met Gly Ala Lys Val Val Glu Ala Thr Pro Asp Trp
290                 295                 300

Gly Asp Pro Ser Glu Ala Met Trp His Gly Ile Trp Val Pro Gly Phe
305                 310                 315                 320

Ala Gly Glu His Asp Met Leu Asp Trp Asp Ala Leu His Gly Gln Val
                325                 330                 335

Asp Glu Asn Leu Ile Glu Leu Ile His Glu Gly Arg Arg Leu Thr Gly
            340                 345                 350

Val Asp Tyr Gly Arg Ala Asp Thr Phe Arg Gly Gly Met Trp Asp Thr
        355                 360                 365

Trp Thr Glu Phe Met Asn Asp Tyr Asp Val Leu Ile Ser Pro Thr Leu
370                 375                 380

Ala Ser Ala Thr Phe Pro Leu Thr Gln Phe Ala Pro Asp Trp Leu Gln
385                 390                 395                 400

Gly Lys Ser Leu Arg Glu Gln Leu Leu Asp Trp Leu Thr Tyr Pro
                405                 410                 415

Tyr Asn Met Leu Asn Asn Pro Ala Ile Thr Val Pro Ala Gly Phe Thr
                420                 425                 430

Pro Asp Gly Arg Pro Val Gly Leu Gln Ile Ala Ala Arg His Arg Gln
            435                 440                 445

Asp Ala Leu Val Leu Arg Val Ala Ala Asn Leu Glu Gln Ala Arg Pro
450                 455                 460

Trp Ala Asp Arg Arg Pro Val Ala
465                 470

<210> SEQ ID NO 3
<211> LENGTH: 1431
<212> TYPE: DNA
<213> ORGANISM: Rhodococcus erythropolis
<220> FEATURE:
<221> NAME/KEY: CDS
<222> LOCATION: (1)..(1431)

<400> SEQUENCE: 3 atg acc gaa cag aat ctg cat tgg ctc tcc gct acc gag atg gcg gcg    48
Met Thr Glu Gln Asn Leu His Trp Leu Ser Ala Thr Glu Met Ala Ala
1               5                   10                  15
```

```
tcg gtc gcg tcg aac agt ctc tcg ccc aac gag att gcc gaa gcg atg      96
Ser Val Ala Ser Asn Ser Leu Ser Pro Asn Glu Ile Ala Glu Ala Met
         20                  25                  30 atc cag cgc gtc gac gct gtc aat ccg tcg atc aac gcg ata gtg cag     144
Ile Gln Arg Val Asp Ala Val Asn Pro Ser Ile Asn Ala Ile Val Gln
             35                  40                  45 ttc gat cgc gag cag gtc acg cgc gac gcg gcc gaa ctc tca cgg caa     192
Phe Asp Arg Glu Gln Val Thr Arg Asp Ala Ala Glu Leu Ser Arg Gln
 50                  55                  60 cag gaa tcg ggc gag aaa ctc ggc ccg ctg cac ggc gtt ccg ttc acg     240
Gln Glu Ser Gly Glu Lys Leu Gly Pro Leu His Gly Val Pro Phe Thr
 65                  70                  75                  80 atc aaa gat ctg acg gca gtc gac ggg ctg ccg acc acg ttc ggg atg     288
Ile Lys Asp Leu Thr Ala Val Asp Gly Leu Pro Thr Thr Phe Gly Met
                 85                  90                  95 aag ccg atg gcc gac aac atc gcg acg gga aat gcc gtc gtc gtg gac     336
Lys Pro Met Ala Asp Asn Ile Ala Thr Gly Asn Ala Val Val Val Asp
            100                 105                 110 agg ctg cgc ggc gcc ggc gga ctg ttc ctg gga aag acg aac act ccc     384
Arg Leu Arg Gly Ala Gly Gly Leu Phe Leu Gly Lys Thr Asn Thr Pro
        115                 120                 125 gaa agc ggt tac tac ggt ggc acg gac aac cac ctg tac ggg ccg acg     432
Glu Ser Gly Tyr Tyr Gly Gly Thr Asp Asn His Leu Tyr Gly Pro Thr
130                 135                 140 cac aac ccg tgg aag ctc ggc aac agc gcg ggc ggg tcc agt ggc ggc     480
His Asn Pro Trp Lys Leu Gly Asn Ser Ala Gly Gly Ser Ser Gly Gly
145                 150                 155                 160 gcg tcg gct gcc gtg gct gca ggc ctc ggg cca ctt gcc gag ggc agt     528
Ala Ser Ala Ala Val Ala Ala Gly Leu Gly Pro Leu Ala Glu Gly Ser
                165                 170                 175 gac ggc gcc gga tcg gtg cgt atc cca tcg gcg ctc tgc ggg gtc gtc     576
Asp Gly Ala Gly Ser Val Arg Ile Pro Ser Ala Leu Cys Gly Val Val
            180                 185                 190 ggg ctc aaa ccg acc acc ggc gtc att ccg cag acc att ctg gcc ggg     624
Gly Leu Lys Pro Thr Thr Gly Val Ile Pro Gln Thr Ile Leu Ala Gly
        195                 200                 205 cgg ttc tac aac tgg gcg tac cac ggt ccg atc acc agg acc gtc gcc     672
Arg Phe Tyr Asn Trp Ala Tyr His Gly Pro Ile Thr Arg Thr Val Ala
210                 215                 220 gac aac gcg ctc atg ctc gac atc atg gcc ggg ccg gac aat gcg gat     720
Asp Asn Ala Leu Met Leu Asp Ile Met Ala Gly Pro Asp Asn Ala Asp
225                 230                 235                 240 ccg ctc tcg atc gag cgt gcg gag acc tcg tac gtc gaa gcg gcg aag     768
Pro Leu Ser Ile Glu Arg Ala Glu Thr Ser Tyr Val Glu Ala Ala Lys
                245                 250                 255 ggt gac gtg aag ggg ctt cgc gtc gcg tgg tcg acg aat ctc ggc ctc     816
Gly Asp Val Lys Gly Leu Arg Val Ala Trp Ser Thr Asn Leu Gly Leu
            260                 265                 270 ggc cat gtt gat ccg gag gtg ctg gcg gtg tgc ctc gac gcg ctg gcg     864
Gly His Val Asp Pro Glu Val Leu Ala Val Cys Leu Asp Ala Leu Ala
        275                 280                 285 gca ttc gag gaa ttg ggt gcc cag atc acc gag gcg acc ccg cag tgg     912
Ala Phe Glu Glu Leu Gly Ala Gln Ile Thr Glu Ala Thr Pro Gln Trp
290                 295                 300 gga aat ccg tcg gag tcg atg tgg aac ggc atc tgg gtt ccc ggt ttc     960
Gly Asn Pro Ser Glu Ser Met Trp Asn Gly Ile Trp Val Pro Gly Phe
305                 310                 315                 320 gct tcc gaa tac gac ttg ctc gac tgg gag aac cag cgc ggc gag gtc    1008
Ala Ser Glu Tyr Asp Leu Leu Asp Trp Glu Asn Gln Arg Gly Glu Val
                325                 330                 335
```

```
gac gac aac ctg atc gag atc atg cac gag gcc gag cgg ctc acc ggt    1056
Asp Asp Asn Leu Ile Glu Ile Met His Glu Ala Glu Arg Leu Thr Gly
            340                 345                 350 gtc gac gtc ggg cgg gcc gac gca ttc cgc ggc gtc atg tgg gac acg    1104
Val Asp Val Gly Arg Ala Asp Ala Phe Arg Gly Val Met Trp Asp Thr
                355                 360                 365 tgg acc acg ttc atg aac gac tac gac gtg ttg gtc tcg ccg acc ttg    1152
Trp Thr Thr Phe Met Asn Asp Tyr Asp Val Leu Val Ser Pro Thr Leu
370                 375                 380 gct tcg gcc acg ttc ccg ctc agt cag ttc gcg ccg tcg tgg ctc gaa    1200
Ala Ser Ala Thr Phe Pro Leu Ser Gln Phe Ala Pro Ser Trp Leu Glu
385                 390                 395                 400 ggt gcg tcg ttg cgt gag cag ttg ctc gat tgg ctc ttc acc tac ccg    1248
Gly Ala Ser Leu Arg Glu Gln Leu Leu Asp Trp Leu Phe Thr Tyr Pro
                405                 410                 415 tac aac atg ctc aac aac ccc gcg atc acc gtg ccc gcc gga ttt acc    1296
Tyr Asn Met Leu Asn Asn Pro Ala Ile Thr Val Pro Ala Gly Phe Thr
                420                 425                 430 gcc gac ggt cga ccg gtg ggg ctg cag atc gcc gca cgc cac cgc cag    1344
Ala Asp Gly Arg Pro Val Gly Leu Gln Ile Ala Ala Arg His Arg Gln
                435                 440                 445 gac gca ctg gtt ctg cgg act gcc gca aac ttc gaa gcg gtg cgt ccg    1392
Asp Ala Leu Val Leu Arg Thr Ala Ala Asn Phe Glu Ala Val Arg Pro
450                 455                 460 tgg gcg gac agg aag ccg gcc gat tca ctg gtg gtg gcc                1431
Trp Ala Asp Arg Lys Pro Ala Asp Ser Leu Val Val Ala
465                 470                 475

<210> SEQ ID NO 4
<211> LENGTH: 477
<212> TYPE: PRT
<213> ORGANISM: Rhodococcus erythropolis

<400> SEQUENCE: 4

Met Thr Glu Gln Asn Leu His Trp Leu Ser Ala Thr Glu Met Ala Ala
1               5                   10                  15

Ser Val Ala Ser Asn Ser Leu Ser Pro Asn Glu Ile Ala Glu Ala Met
                20                  25                  30

Ile Gln Arg Val Asp Ala Val Asn Pro Ser Ile Asn Ala Ile Val Gln
            35                  40                  45

Phe Asp Arg Glu Gln Val Thr Arg Asp Ala Ala Glu Leu Ser Arg Gln
    50                  55                  60

Gln Glu Ser Gly Glu Lys Leu Gly Pro Leu His Gly Val Pro Phe Thr
65                  70                  75                  80

Ile Lys Asp Leu Thr Ala Val Asp Gly Leu Pro Thr Thr Phe Gly Met
                85                  90                  95

Lys Pro Met Ala Asp Asn Ile Ala Thr Gly Asn Ala Val Val Val Asp
            100                 105                 110

Arg Leu Arg Gly Ala Gly Gly Leu Phe Leu Gly Lys Thr Asn Thr Pro
        115                 120                 125

Glu Ser Gly Tyr Tyr Gly Gly Thr Asp Asn His Leu Tyr Gly Pro Thr
    130                 135                 140

His Asn Pro Trp Lys Leu Gly Asn Ser Ala Gly Gly Ser Ser Gly Gly
145                 150                 155                 160

Ala Ser Ala Ala Val Ala Ala Gly Leu Gly Pro Leu Ala Glu Gly Ser
                165                 170                 175

Asp Gly Ala Gly Ser Val Arg Ile Pro Ser Ala Leu Cys Gly Val Val
            180                 185                 190
```

```
Gly Leu Lys Pro Thr Thr Gly Val Ile Pro Gln Thr Ile Leu Ala Gly
        195                 200                 205

Arg Phe Tyr Asn Trp Ala Tyr His Gly Pro Ile Thr Arg Thr Val Ala
    210                 215                 220

Asp Asn Ala Leu Met Leu Asp Ile Met Ala Gly Pro Asp Asn Ala Asp
225                 230                 235                 240

Pro Leu Ser Ile Glu Arg Ala Glu Thr Ser Tyr Val Glu Ala Ala Lys
                245                 250                 255

Gly Asp Val Lys Gly Leu Arg Val Ala Trp Ser Thr Asn Leu Gly Leu
                260                 265                 270

Gly His Val Asp Pro Glu Val Leu Ala Val Cys Leu Asp Ala Leu Ala
            275                 280                 285

Ala Phe Glu Glu Leu Gly Ala Gln Ile Thr Glu Ala Thr Pro Gln Trp
    290                 295                 300

Gly Asn Pro Ser Glu Ser Met Trp Asn Gly Ile Trp Val Pro Gly Phe
305                 310                 315                 320

Ala Ser Glu Tyr Asp Leu Leu Asp Trp Glu Asn Gln Arg Gly Glu Val
                325                 330                 335

Asp Asp Asn Leu Ile Glu Ile Met His Glu Ala Glu Arg Leu Thr Gly
            340                 345                 350

Val Asp Val Gly Arg Ala Asp Ala Phe Arg Gly Val Met Trp Asp Thr
        355                 360                 365

Trp Thr Thr Phe Met Asn Asp Tyr Asp Val Leu Val Ser Pro Thr Leu
    370                 375                 380

Ala Ser Ala Thr Phe Pro Leu Ser Gln Phe Ala Pro Ser Trp Leu Glu
385                 390                 395                 400

Gly Ala Ser Leu Arg Glu Gln Leu Leu Asp Trp Leu Phe Thr Tyr Pro
                405                 410                 415

Tyr Asn Met Leu Asn Asn Pro Ala Ile Thr Val Pro Ala Gly Phe Thr
                420                 425                 430

Ala Asp Gly Arg Pro Val Gly Leu Gln Ile Ala Ala Arg His Arg Gln
        435                 440                 445

Asp Ala Leu Val Leu Arg Thr Ala Ala Asn Phe Glu Ala Val Arg Pro
450                 455                 460

Trp Ala Asp Arg Lys Pro Ala Asp Ser Leu Val Val Ala
465                 470                 475
```

AMIDASE AND USE THEREOF FOR PRODUCING 3-AMINOCARBOXYLIC ACID ESTERS

RELATED APPLICATIONS

This application is a divisional of U.S. application Ser. No. 13/497,985, filed Mar. 23, 2012, which is a national stage application (under 35 U.S.C. §371) of PCT/EP2010/064098, filed Sep. 24, 2010, which claims benefit of European Application No. 09171414.7, filed Sep. 25, 2009, the entire contents of each of which are hereby incorporated by reference in this application.

SEQUENCE LISTING

The Sequence Listing associated with this application is filed in electronic format via EFS-Web and is hereby incorporated by reference into the specification in its entirety. The name of the text file containing the Sequence Listing is Sequence_Listing__12810__01547_US. The size of the text file is 22 KB, and the text file was created on Jul. 15, 2013.

DESCRIPTION

The present invention relates to a new amidase and use thereof for producing optically active 3-aminocarboxylic acid ester compounds, and derivatives thereof.

Asymmetric synthesis, i.e. reactions in which a chiral group is produced from a prochiral group, so that the stereoisomeric products (enantiomers or diastereomers) are formed in unequal amounts, has become tremendously important chiefly in the pharmaceutical industry, as often only a particular optically active isomer is therapeutically active. In this connection, optically active intermediates of the active compounds are also becoming increasingly important. This also applies to 3-aminocarboxylic acid esters (Formula I), and derivatives thereof.

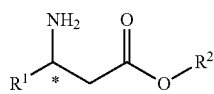

(Formula I)

Therefore there is a great need for effective synthesis routes for producing optically active compounds of general formula I.

WO 97/41214 describes biocatalysts with aminoacylase activity, which do not have lipase or esterase activity.

WO 2008/003761 describes a process for producing optically active 3-aminocarboxylic acid esters in which an enantiomeric mixture of a simply N-acylated 3-aminocarboxylic acid ester, enriched in one enantiomer, is submitted, by adding an acidic salt-forming substance, to a deacylation and a subsequent further enantiomeric enrichment by crystallization.

The problem to be solved by the present invention is therefore to provide a simple and therefore economical process for producing optically active 3-aminocarboxylic acid esters and derivatives thereof.

Surprisingly, it was found that the above problem is solved by a process for producing optically active 3-aminocarboxylic acid ester compounds of general Formula I, and the ammonium salts thereof,

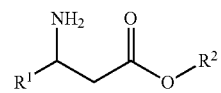

(I)

in which $R^1$ stands for alkyl, alkoxyalkyl, alkenyl, cycloalkyl, heterocycloalkyl, aryl, or hetaryl, and $R^2$ stands for alkyl, cycloalkyl or aryl, wherein an enantiomeric mixture of a simply N-acylated 3-aminocarboxylic acid ester of general formula (I.b),

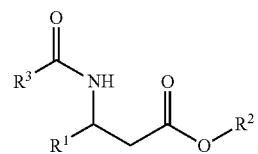

(I.b)

in which $R^1$ and $R^2$ have the meanings given above and $R^3$ stands for hydrogen, alkyl, cycloalkyl or aryl, is submitted, by adding a polypeptide according to claim 1 or 2, to an enantioselective deacylation.

The invention further relates to a process for producing optically active 3-aminocarboxylic acid ester compounds of general Formula I', and derivatives thereof,

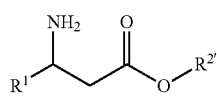

(I')

in which $R^1$ stands for alkyl, alkoxyalkyl, alkenyl, cycloalkyl, heterocycloalkyl, aryl, or hetaryl, and $R^2$ stands for hydrogen, a cation equivalent M+, alkyl, cycloalkyl or aryl, in which a) a β-ketoester of general Formula I.1

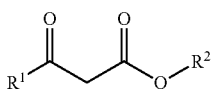

(I.1)

in which $R^1$ and $R^2$ have the meanings given above, is reacted a1) with at least one carboxylic acid amide of formula $R^3$—C(O)NH$_2$, in which $R^3$ has the meaning given above, in the presence of an amidation catalyst, or a2) with ammonia and then with a carboxylic acid derivative of formula $R^3$—C(O)X, in which X stands for halogen or a residue of formula OC(O)$R^4$, in which $R^4$ has the meaning given above for $R^3$, obtaining the corresponding N-acylated, α-unsaturated (Z)-3-aminocarboxylic acid ester, of general formula (I.a),

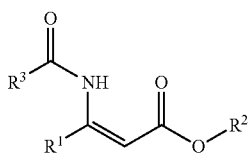

(I.a)

in which $R^1$, $R^2$ and $R^3$ have the meanings given above, b) the enamide (I.a) obtained in this reaction is submitted to a hydrogenation, obtaining an enantiomeric mixture of simply N-acylated β-aminocarboxylic acid esters of general formula (I.b),

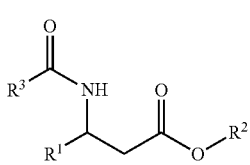

(I.b)

in which $R^1$, $R^2$ and $R^3$ have the meanings given above, c) the enantiomeric mixture of compounds I.b obtained in the hydrogenation is submitted, by adding a polypeptide with amidase activity, to an enantioselective deacylation and the resultant ammonium salt of a 3-aminocarboxylic acid ester, enriched with respect to a stereoisomer, is isolated, and d) optionally the ammonium salt isolated is converted to the 3-aminocarboxylic acid ester, and e) optionally the 3-aminocarboxylic acid ester is converted to the free 3-aminocarboxylic acid or a salt thereof.

The invention further relates to a polypeptide with amidase activity, selected from a) polypeptide comprising an amino acid sequence according to SEQ ID NO: 2, and b) polypeptide comprising an amino acid sequence that has at least 96%, preferably 98%, especially preferably 99% identity with SEQ ID NO:2.

The invention further relates to a polypeptide with amidase activity, selected from c) polypeptide comprising an amino acid sequence according to SEQ ID NO: 4, and d) polypeptide comprising an amino acid sequence that has at least 80%, preferably 85, 88%, 90%, especially preferably 92%, 94%, 96%, 98%, 99% identity with SEQ ID NO:4.

Figure 1:
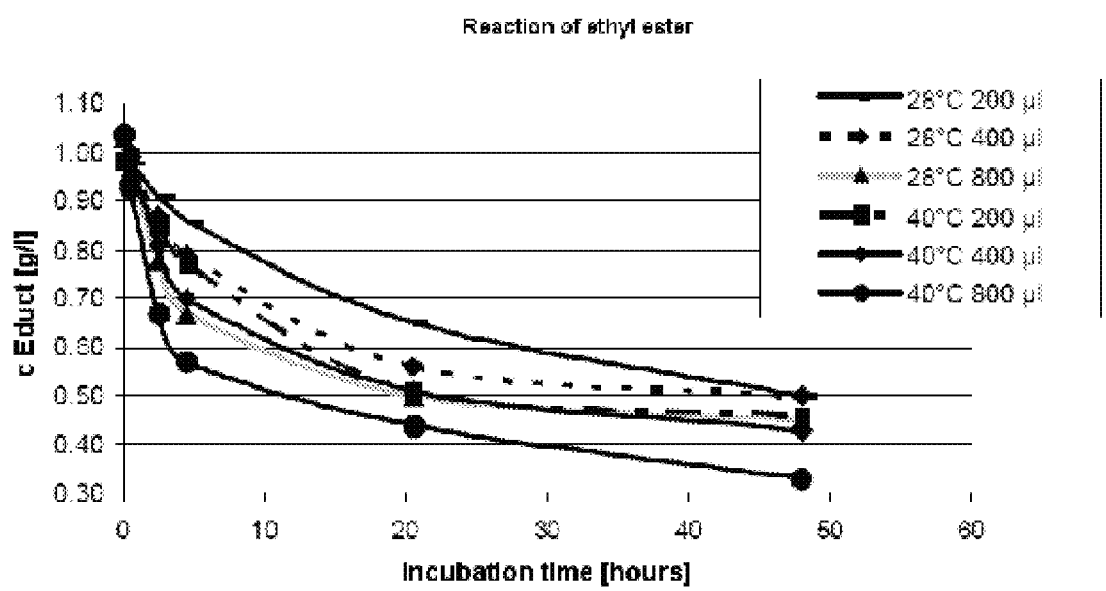
FIG. 1 shows the formation of 3-acetylamino-3-phenyl-propionic acid ethyl ester as a function of reaction time and temperature.

"Chiral compounds" are, in the context of the present invention, compounds with at least one chiral centre (i.e. at least one asymmetric atom, e.g. at least one asymmetric carbon atom or phosphorus atom), with chiral axis, chiral plane or helical shape. The term "chiral catalyst" comprises catalysts that have at least one chiral ligand.

"Achiral compounds" are compounds that are not chiral.

"Prochiral compound" means a compound with at least one prochiral centre. "Asymmetric synthesis" denotes a reaction in which, from a compound with at least one prochiral centre, a compound is produced with at least one chiral centre, a chiral axis, chiral plane or helical shape, wherein the stereoisomeric products form in unequal amounts.

"Stereoisomers" are compounds with the same constitution but with different atomic arrangement in three-dimensional space.

"Enantiomers" are stereoisomers that relate to one another as object to mirror image. The "enantiomeric excess" (ee) achieved in an asymmetric synthesis can be found from the following formula:

$$ee[\%]=(R-S)/(R+S)*100.$$

R and S are the descriptors of the CIP system for the two enantiomers and represent the absolute configuration on the asymmetric atom. The enantiomerically pure compound (ee=100%) is also known as "homochiral compound".

The process according to the invention leads to products that are enriched with respect to a particular stereoisomer. The "enantiomeric excess" (ee) achieved is as a rule at least 95%, preferably at least 98% and especially preferably at least 99%.

"Diastereomers" are stereoisomers that are not enantiomeric to one another.

Although further asymmetric atoms can be present in the compounds covered by the present invention, the stereochemical concepts presented herein refer, unless expressly stated otherwise, to the carbon atom of the respective compounds corresponding to the asymmetric β-carbon atom in compound I or I'. If further stereocentres are present, they are ignored in the naming in the context of the present invention.

Hereinafter, the expression "alkyl" comprises linear and branched alkyl groups. Preferably they are linear or branched $C_1$-$C_{20}$-alkyl, preferably $C_1$-$C_{12}$-alkyl, especially preferably $C_1$-$C_8$-alkyl and quite especially preferably $C_1$-$C_6$-alkyl groups. Examples of alkyl groups are in particular methyl, ethyl, propyl, isopropyl, n-butyl, isobutyl, sec.-butyl, tert.-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-methylheptyl, nonyl, decyl, 2-propylheptyl.

The expression "alkyl" also comprises substituted alkyl groups, which can generally carry 1, 2, 3, 4 or 5, preferably 1, 2 or 3 and especially preferably 1 substituents, selected from the groups cycloalkyl, aryl, hetaryl, halogen, $COOR^f$, $COO^-M^+$ and $NE^1E^2$, wherein $R^f$ stands for hydrogen, alkyl, cycloalkyl or aryl, $M^+$ stands for a cation equivalent and $E^1$, and $E^2$, independently of one another, stand for hydrogen, alkyl, cycloalkyl or aryl.

The expression "alkoxyalkyl" comprises linear and branched alkyl groups that are linked to an alkoxy residue. The alkoxy residue can also be linear or branched. Preferably they are linear or branched $C_1$-$C_{20}$-alkyl, preferably $C_1$-$C_{12}$-alkyl, especially preferably $C_1$-$C_8$-alkyl and quite especially preferably $C_1$-$C_6$-alkyl groups, which are linked $C_1$-$C_{12}$-alkoxy, especially preferably $C_1$-$C_6$-alkoxy residues. Examples of alkyl groups are mentioned above; examples of alkoxy groups are in particular methoxy, ethoxy, propoxy, isopropoxy, n-butoxy, isobutoxy, sec.-butoxy. Examples of alkoxyalkyls are in particular methoxymethyl, ethoxymethyl, ethoxyethyl, ethoxypropyl.

The expression "alkenyl" comprises linear and branched alkyl groups, which still bear at least one C=C double bond. Preferably they are linear $C_1$-$C_{20}$-alkyl groups, bearing a C=C double bond. Examples of alkenyl groups are in particular 1-propenyl, 1-butenyl, 1-pentenyl, 1-hexenyl.

The expression "cycloalkyl" comprises, in the sense of the present invention, both unsubstituted and substituted cycloalkyl groups, preferably $C_3$-$C_8$-cycloalkyl groups, such as cyclopentyl, cyclohexyl or cycloheptyl, which in the case of a substitution can generally bear 1, 2, 3, 4 or 5, preferably 1, 2 or 3 and especially preferably 1 substituents, preferably selected from alkyl and the substituents mentioned for alkyl.

The expression "heterocycloalkyl" comprises, in the sense of the present invention, saturated cycloaliphatic groups generally with 4 to 7, preferably 5 or 6 ring atoms, in which 1 or 2 of the ring carbon atoms are replaced with heteroatoms, preferably selected from the elements oxygen, nitrogen and sulphur, and which optionally can be substituted, wherein in the case of a substitution, these heterocycloaliphatic groups can bear 1, 2 or 3, preferably 1 or 2, especially preferably 1 substituents, selected from alkyl, cycloalkyl, aryl, $COOR^f$, $COO^-M^+$ and $NE^1E^2$, preferably alkyl, wherein $R^f$ stands for hydrogen, alkyl, cycloalkyl or aryl, $M^+$ stands for a cation equivalent and $E^1$ and $E^2$ independently of one another stand for hydrogen, alkyl, cycloalkyl or aryl. As examples of these heterocycloaliphatic groups we may mention pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

The expression "aryl" comprises, in the sense of the present invention, unsubstituted and substituted aryl groups, and preferably stands for phenyl, tolyl, xylyl, mesityl, naphthyl, fluorenyl, anthracenyl, phenanthrenyl or naphthacenyl, especially preferably for phenyl or naphthyl, wherein these aryl groups in the case of a substitution can generally bear 1, 2, 3, 4 or 5, preferably 1, 2 or 3 and especially preferably 1 substituents, selected from the groups alkyl, alkoxy, nitro, cyano or halogen.

The expression "hetaryl" comprises, in the sense of the present invention, unsubstituted or substituted, heterocycloaromatic groups, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl, wherein these heterocycloaromatic groups can, in the case of a substitution, generally bear 1, 2 or 3 substituents, selected from the groups alkyl, alkoxy, acyl, carboxyl, carboxylate, —$SO_3H$, sulphonate, $NE^1E^2$, alkylene-$NE^1E^2$ or halogen, wherein $E^1$ and $E^2$ have the meanings given above.

The above explanations for the expressions "alkyl", "cycloalkyl", "aryl", "heterocycloalkyl" and "hetaryl" apply correspondingly for the expressions "alkoxy", "cycloalkoxy", "aryloxy", "heterocycloalkoxy" and "hetaryloxy".

The expression "acyl" stands, in the sense of the present invention, for alkanoyl or aroyl groups generally with 2 to 11, preferably 2 to 8 carbon atoms, for example for the acetyl, propanoyl, butanoyl, pentanoyl, hexanoyl, heptanoyl, 2-ethylhexanoyl, 2-propylheptanoyl, benzoyl, naphthoyl or trifluoroacetyl group.

"Halogen" stands for fluorine, chlorine, bromine and iodine, preferably for fluorine, chlorine and bromine.

$M^+$ stands for a cation equivalent, i.e. a monovalent cation or the unipositive component of the charge of a multiple cation. This includes e.g. Li, Na, K, Ca and Mg.

The processes according to the invention make possible, as already described, the production of optically active compounds of general Formula I, and the production of derivatives thereof.

$R^1$ preferably stands for $C_1$-$C_6$-alkyl, 1-$C_3$-$C_6$-alkenyl, or $C_6$-$C_{14}$-aryl, which can optionally be substituted, as mentioned at the beginning. In particular $R^1$ stands for methyl, ethyl, n-propyl, isopropyl, n-butyl, tert.-butyl, 1-propenyl, 1-heptenyl, or phenyl, especially for methyl and phenyl.

$R^2$ preferably stands for unsubstituted or substituted $C_1$-$C_6$-alkyl, $C_3$-$C_7$-cycloalkyl or $C_6$-$C_{14}$-aryl. Especially preferred $R^2$ residues are methyl, ethyl, n-propyl, isopropyl, n-butyl, tert.-butyl, trifluoromethyl, cyclohexyl, phenyl and benzyl.

$R^{2'}$ stands for hydrogen, $M^+$, and for the meanings stated for $R^2$.

$R^3$ stands for hydrogen, alkyl, cycloalkyl or aryl, in particular for hydrogen, methyl, ethyl, trifluoromethyl, benzyl and phenyl.

According to the invention, an enantiomeric mixture of compounds I.b is submitted, by adding an amidase, to an enantioselective deacylation and the resultant ammonium salt of a 3-aminocarboxylic acid ester, enriched with respect to a stereoisomer, is isolated.

It is a characteristic feature of the process according to the invention that the isomeric mixture of compounds of general Formula I.b used for the deacylation also comprises the corresponding enantiomer, or starting from chiral β-ketoesters also diastereomers in non-negligible amounts. Advantageously, the process therefore makes possible the production of optically active compounds of general Formula I, starting from isomeric mixtures of compounds of general Formula I.b, such as are obtainable for example from the precursor compounds by usual asymmetric hydrogenation of enamides.

Usually, in this process step, enantiomeric mixtures are used that comprise the enantiomers in the same molar ratio or else are already enriched in one enantiomer. The ee value of these mixtures is preferably above 75% and especially preferably above 90%. Depending on the conditions selected for the hydrogenation of the enamide (I.a), racemates or mixtures already enriched in one enantiomer are produced. In order to obtain mixtures that are already enriched in one enantiomer, as a rule enantioselective hydrogenation processes are chosen, for example such as are mentioned in WO 2008/003761, whose description is expressly included here by reference.

The deacylation is preferably carried out at a temperature of 20-40° C., especially preferably between 20 and 30° C. The reaction is usually carried out in an aqueous buffer.

The invention further relates to a process comprising the reaction stages a) to c) and optionally d) and e) described below.

Stage a)

In one embodiment of stage a) of the process according to the invention a β-ketoester of Formula I.1 is reacted with at least one carboxylic acid amide of formula $R^3$—C(O)$NH_2$, in the presence of an amidation catalyst with removal of the reaction water, to a 3-aminocarboxylic acid ester of Formula I.a (step a.1).

Preferably, in step a.1, the carboxylic acid amides of formula $R^3$—$C(O)NH_2$ are acetamide, propionic acid amide, benzoic acid amide, formamide or trifluoroacetamide, in particular benzoic acid amide or acetamide.

Solvents suitable for step a.1 are those that form a low-boiling azeotrope with water, from which the reaction water can be removed by separation techniques (e.g. azeotropic distillation) known by a person skilled in the art. In particular they are aromatics, such as toluene, benzene, etc., ketones, such as methyl isobutyl ketone or methyl ethyl ketone etc. and haloalkanes, such as chloroform. Preferably toluene is used.

Suitable amidation catalysts are for example acids, such as p-toluenesulphonic acid, methanesulphonic acid, sulphuric acid or the like. p-Toluenesulphonic acid is preferably used.

Preferably the reaction in process step a.1 takes place at a temperature in the range from 20 to 110° C., especially preferably 60 to 90° C. Especially preferably, the temperature is above the boiling point of the solvent used under S.T.P.

Process step a.1 is usually carried out at a pressure from 0.01 to 1.5 bar, in particular 0.1 to 0.5 bar. Optionally the aminocarboxylic acid ester obtained in step a.1 can be submitted to a purification by usual methods known by a person skilled in the art, e.g. by distillation.

In an alternative embodiment a β-ketoester of Formula I.1 is reacted with aqueous ammonia and then with a carboxylic acid derivative of formula $R^3$—$C(O)X$ to the N-acylated, β-unsaturated (Z)-3-aminocarboxylic acid ester (I.a), in which X stands for halogen or a residue of formula $OC(O)R^4$, in which $R^4$ has the meaning given above for $R^3$ (step a.2).

The carboxylic acid derivative is preferably selected from carboxylic acid chlorides, wherein X stands for chlorine and $R^3$ has the meaning given above, or carboxylic acid anhydrides, wherein X stands for $OC(O)R^4$ and $R^4$ preferably has the same meaning as $R^3$, especially preferably the carboxylic acid derivatives are acetyl chloride, benzoyl chloride or acetic anhydride.

Preferably the acylation in step a.2 is carried out at a temperature in the range from 20° C. to 120° C., especially preferably at a temperature in the range from 60° C. to 90° C.

The acylation in step a.2 is carried out in a polar solvent or a mixture of a polar solvent with a nonpolar solvent, preferably the polar solvent is a carboxylic acid of formula $R^3COOH$ or a tertiary amine, haloalkanes and aromatics are suitable in particular as nonpolar solvent, especially preferably acetic acid or triethylamine is used as solvent.

The acylation in step a.2 can be carried out using a catalyst, this can be used both in catalytic amounts and stoichiometrically or as solvent, non-nucleophilic bases are preferred, such as tertiary amines, especially preferably these are triethylamine and/or dimethylaminopyridine (DMAP).

Optionally in steps a.1 and a.2 the (Z)-3-aminocarboxylic acid ester will be obtained as a mixture with the (E)-3-aminocarboxylic acid ester and optionally further acylation products. In this case the (Z)-3-aminocarboxylic acid ester of Formula I.a will be isolated by methods known by a person skilled in the art. A preferred method is separation by distillation.

Stage b)

The α-unsaturated (Z)-3-aminocarboxylic acid ester compounds of Formula I.a obtained in stage a) can then be submitted to a hydrogenation, optionally an enantioselective hydrogenation, in the presence of an optionally chiral hydrogenation catalyst, obtaining a racemate or an enantiomeric mixture of simply N-acylated β-aminocarboxylic acid esters of general formula (I.b) enriched in one enantiomer.

Preferably at least one complex of a transition metal of groups 8 to 11 of the periodic table of the elements, which comprises at least one chiral, phosphorus atom-containing compound as ligand, is used as hydrogenation catalyst in stage b).

For hydrogenation, preferably a chiral hydrogenation catalyst is used, which is capable of hydrogenating the α-unsaturated, N-acylated 3-aminocarboxylic acid ester (I.a) used preferentially for the desired isomer. Preferably the compound of Formula I.b obtained in stage b) has, after the asymmetric hydrogenation, an ee value of at least 75%, especially preferably at least 90%. However, such a high enantiomeric purity is often not necessary in the process according to the invention, because according to the process of the invention, further enantiomeric enrichment takes place in the subsequent deacylation step. Preferably, however, the ee value of compound I.b is at least 75%.

Preferably the process according to the invention makes enantioselective hydrogenation possible at substrate/catalyst ratios (s/c) of at least 1000:1, especially preferably at least 5000:1 and in particular at least 15000:1.

Preferably a complex of a metal of group 8, 9 or 10 with at least one of the ligands stated hereunder is used for the asymmetric hydrogenation. Preferably the transition metal is selected from Ru, Rh, Ir, Pd or Pt. Catalysts based on Rh and Ru are especially preferred. Rh catalysts are preferred in particular.

The phosphorus-containing compound used as ligand is preferably selected from bidentate and multidentate phosphine, phosphinite, phosphonite, phosphoramidite and phosphite compounds.

Catalysts are preferred for hydrogenation that have at least one ligand selected from the compounds of the following formulae,

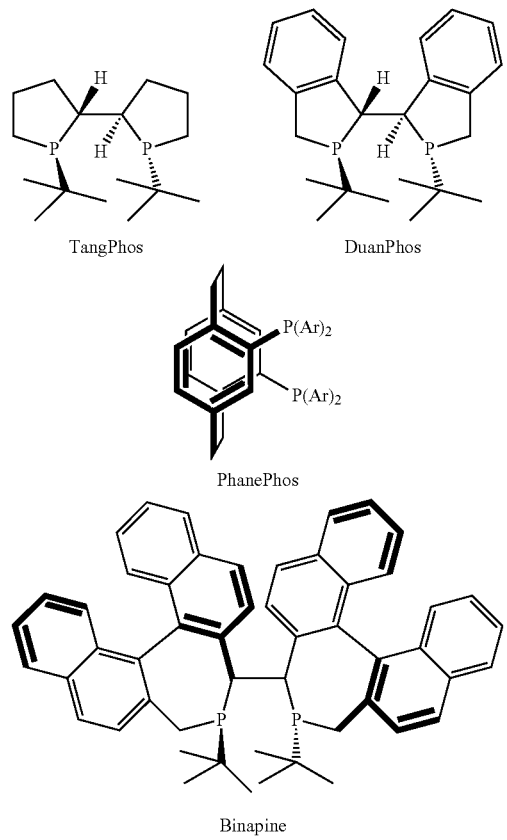

-continued

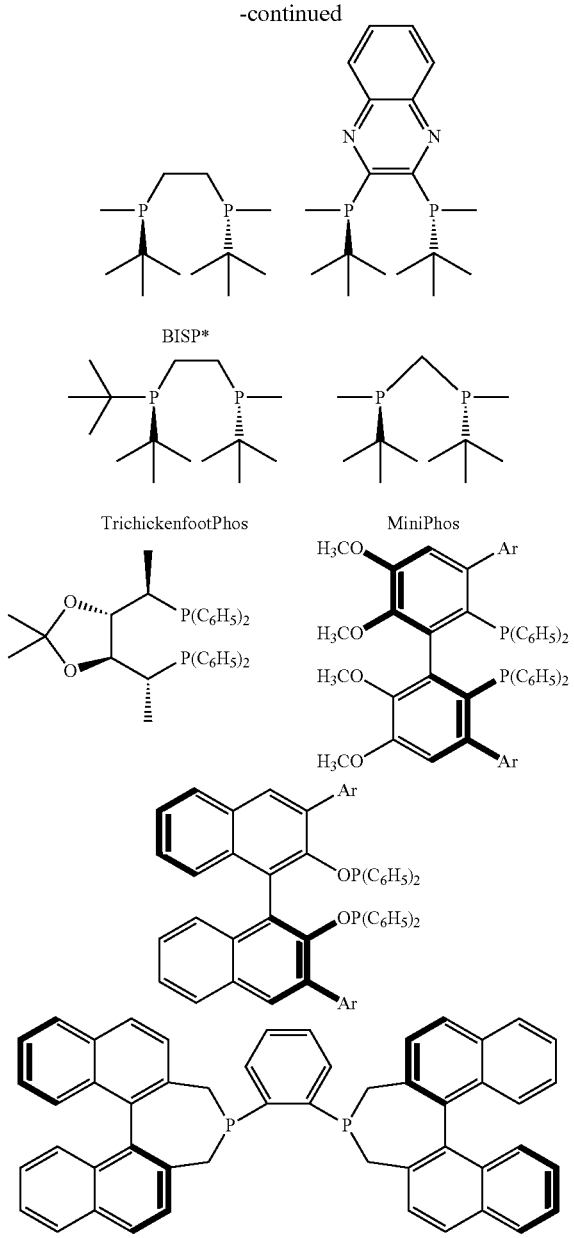

or enantiomers thereof, wherein Ar stands for optionally substituted phenyl, preferably for tolyl or xylyl.

Bidentate compounds of the aforementioned classes of compounds are especially preferred. P-chiral compounds, such as DuanPhos, TangPhos or Binapine are preferred in particular.

Suitable chiral ligands coordinating to the transition metal via at least one phosphorus atom are known by a person skilled in the art and for example are commercially available from Chiral Quest ((Princeton) Inc., Monmouth Junction, N.J.). The nomenclature of the examples of chiral ligands given above corresponds to their commercial designation.

Chiral transition-metal complexes can be obtained in a manner known by a person skilled in the art (e.g. Uson, Inorg. Chim. Acta 73, 275 1983, EP-A-0 158 875, EP-A-437 690) by reaction of suitable ligands with complexes of the metals that comprise labile or hemilabile ligands. In this case, complexes such as $Pd_2$(dibenzylideneacetone)$_3$, $Pd(OAc)_2$ (Ac=acetyl), $RhCl_3$, $Rh(OAc)_3$, $[Rh(COD)Cl]_2$, $[Rh(COD)OH]_2$, $[Rh(COD)OMe]_2$ (Me=methyl), $Rh(COD)$acac, $Rh_4(CO)_{12}$, $Rh_6(CO)_{16}$, $[Rh(COD)_2]X$, $Rh(acac)(CO)_2$ (acac=acetylacetonato), $RuCl_3$, $Ru(acac)_3$, $RuCl_2(COD)$, $Ru(COD)$(methallyl)$_2$, $Ru(Ar)I_2$ and $Ru(Ar)Cl_2$, Ar=aryl, both unsubstituted and substituted, $[Ir(COD)Cl]_2$, $[Ir(COD)_2]X$, Ni(allyl)X can be used as precatalysts. Instead of COD (=1,5-cyclooctadiene) it is also possible to use NBD (=norbornadiene). $[Rh(COD)Cl]_2$, $[Rh(COD)_2]X$, $Rh(acac)(CO)_2$, $RuCl_2(COD)$, $Ru(COD)$(methallyl)$_2$, $Ru(Ar)Cl_2$, Ar=aryl, both unsubstituted and substituted, and the corresponding systems with NBD instead of COD, are preferred. $[Rh(COD)_2]X$ and $[Rh(NBD)_2]X$ are especially preferred.

X can be any anion known by a person skilled in the art, generally unstable in asymmetric synthesis. Examples of X are halogens such as $Cl^-$, $Br^-$ or $I^-$, $BF_4^-$, $ClO_4^-$, $SbF_6^-$, $PF_6^-$, $CF_3SO_3^-$, $BAr_4^-$. $BF_4^-$, $PF_6^-$, $CF_3SO_3^-$, $SbF_6^-$ are preferred for X.

The chiral transition-metal complexes can either be produced in situ in the reaction vessel before the actual hydrogenation reaction or can be produced separately, isolated and then used. It may happen that at least one solvent molecule adds onto the transition-metal complex. The common solvents (e.g. methanol, diethyl ether, tetrahydrofuran (THF), dichloromethane, etc.) for the preparation of complexes are known by a person skilled in the art.

Phosphine-, phosphinite-, phosphonite-, phosphoramidite- and phosphite-metal or -metal-Solv-complexes (Solv=solvent) together with at least one labile or hemilabile ligand are suitable precatalysts, from which the actual catalyst is generated under the hydrogenation conditions.

The hydrogenation step (step b) of the process according to the invention is as a rule carried out at a temperature from −10 to 150° C., preferably at 0 to 120° C. and especially preferably at 10 to 70° C.

The hydrogen pressure can be varied in a range between 0.1 bar and 600 bar. Preferably it is in a pressure range from 0.5 to 20 bar, especially preferably between 1 and 10 bar.

All solvents for asymmetric hydrogenation known by a person skilled in the art are suitable as solvents for the hydrogenation reaction of the enamides I.a. Preferred solvents are lower alkyl alcohols such as methanol, ethanol, isopropanol, and toluene, THF, ethyl acetate. Especially preferably, ethyl acetate or THF is used as solvent in the process according to the invention.

The hydrogenation catalysts (or hydrogenation precatalysts) described above can also be immobilized in a suitable way, e.g. by attachment via functional groups suitable as anchor groups, adsorption, grafting, etc., on a suitable support, e.g. of glass, silica gel, synthetic resins, polymer supports, etc. They are then also suitable for use as solid-phase catalysts. Advantageously, catalyst consumption can be lowered further by these methods. The catalysts described above are also suitable for a continuous reaction, e.g. after immobilization, as described above, in the form of solid-phase catalysts.

In another embodiment the hydrogenation in stage b is carried out continuously. Continuous hydrogenation can take place in one or preferably in several reaction zones. Several reaction zones can be formed by several reactors or by spatially different regions within one reactor. When several reactors are used, they can be identical or different. They can in each case have identical or different mixing characteristics and/or can be subdivided once or more by internal fittings. The reactors can be connected together in any way, e.g. in parallel or in series.

Suitable pressure-proof reactors for hydrogenation are known by a person skilled in the art. These include the generally usual reactors for gas-liquid reactions, for example tubular reactors, shell-and-tube reactors, stirred reactors, gas circulating reactors, bubble columns, etc., which can optionally be filled or subdivided by internal fittings.

Step c)

In process step c) the enantiomeric mixture of compounds I.b obtained in the hydrogenation is submitted to an enantioselective deacylation by adding a polypeptide with amidase activity and the resultant ammonium salt of a 3-aminocarboxylic acid ester, enriched with respect to a stereoisomer, is isolated. The polypeptide with amidase activity can be used as purified enzyme, as partially purified raw extract or in the form of a living or killed microorganism, which contains the amidase. Preferred amidases are those with the primary structure SEQ ID NO:2 or NO:4 or variants of SEQ ID NO:2 or NO:4, which are obtained by insertion, deletion or substitution of a few amino acids, preferably 1-20, especially preferably 1-10 amino acids.

The reaction usually takes place in aqueous buffer. The resultant reaction product can be purified and isolated by usual methods.

Step d)

If desired, the ammonium salts isolated in the enantiomer-enriching deacylation by amidase reaction can be submitted to further processing. Thus, it is possible, for example, for releasing the optically active compound of Formula I, to bring the product of crystallization into contact with a suitable base, preferably $NaHCO_3$, NaOH, KOH. In a suitable procedure, the product of deacylation is dissolved or suspended in water and then the pH is adjusted by addition of base to about 8 to 12, preferably about 10. For isolating the free 3-aminocarboxylic acid ester it is possible to extract the basic solution or suspension with a suitable organic solvent, e.g. an ether, such as methyl butyl ether, a hydrocarbon or hydrocarbon mixture, e.g. an alkane, such as pentane, hexane, heptane, or an alkane mixture, naphtha or petroleum ether, or aromatics, such as toluene. A preferred extractant is toluene. In this procedure, the 3-amino acid ester can be obtained almost quantitatively, while also maintaining the ee value.

which $R^{2'}$ is hydrogen, salts of the free carboxylic acid, in which $R^{2'}$ is $M^+$, and optically active 3-aminoalcohols.

The invention further relates to polypeptides that can catalyse an amidase reaction, and comprise the following primary structure (amino acid sequence):
SEQ ID NO:2
or a polypeptide sequence that has at least 96%, preferably 98%, especially preferably 99% identity with SEQ ID NO:2.
SEQ ID NO:4
or a polypeptide sequence that has at least 80%, preferably at least 85%, especially preferably at least 95% identity with SEQ ID NO:4.

The following model reaction is understood as amidase reaction in the sense of this invention:

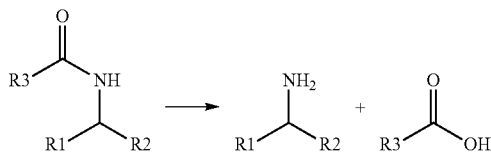

wherein R1 and R3 in each case stand for methyl and R2 stands for ethyl.

The following reaction conditions were selected:
200 μl cells
50 μl 1 M $KH_2PO_4$ buffer pH 7.0
1-10 g/L substrate racemic or S-enantiomer-enriched
740 μl $H_2O$.

For culture of the cells, see example 2.

The amidase with SEQ ID NO:2 can for example be isolated by cloning from *Rhodococcus equi* DSM 19590.

Example 1

Cloning of an Amidase from *Rhodococcus equi*

The coding region of the S-selective amidase from *Rhodococcus equi* was amplified by PCR with the following oligonucleotide primers:

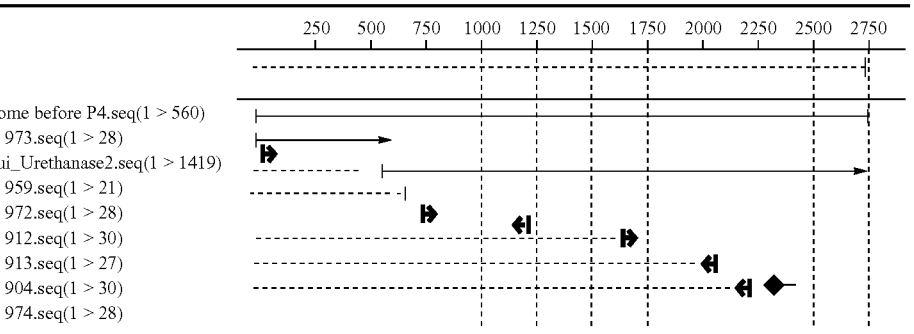

Step e)

Optionally the 3-aminocarboxylic acid esters can be derivatized using methods known by a person skilled in the art. Possible derivatizations comprise for example saponification of the ester or stereoselective reduction of the carboxylcarbon atom to an optically active alcohol.

Derivatives of compounds of Formula I' according to the invention therefore comprise for example ammonium salts of the 3-aminocarboxylic acid esters, the free carboxylic acid in

```
Mke 973   GTCAGATGGATCCTCATGGCACTTCTTC

Mke 959   ATCTCCTCTGCGATCTCGTTG

Mke 972   GTTCACGATCAAGGACCTCACCGACGTC

Mke 912   GCCGTGGTAGGCCCAGTTGTTGTAGCGGCC
```

-continued

```
Mke 913  CGACGTCCTCATCTCGCCGACCCTCGC

Mke 904  CTACGCCACAGGACGACGGTCCGCCCACGG

Mke 974  CTGGTCCCCACTGCGTCGGTAGGTGATC
```

In order to insert the corresponding cleavage sites for cloning, the sequence obtained in this way was amplified in another PCR with the following primers:

```
5'-GGGATACTCATATGAGTACATCGGATCCGGG-3'

3'-GAGTCTCAAGCTTACGCCACCGGTCGACGATCC-5'
```

*Rhodococcus equi* is a soil isolate, which was isolated from screening for 3-acetylamino-3-phenyl-propionic-acid ethyl esters. The strain was determined at the DSMZ. The strain was deposited at the DSM under No. 19590.

The genomic DNA was obtained by means of a Qiagen kit:
For isolation of chromosomal DNA from *Rhodococcus equi*, a bacterial culture was inoculated in 30 ml FP medium and incubated overnight at 30° C.

The culture was centrifuged at 5000×g and 22 µl RNase A solution was added to an 11 ml aliquot of B1 buffer. The cell pellet was resuspended in each case with 11 ml RNase-containing B1 buffer. Then 300 ml of lysozyme stock solution (100 mg/ml) and 500 µl of proteinase-K stock solution (20 mg/ml) were added and, for lysis of the cells, incubated at 37° C. for 30 min. Meanwhile, a QIAGEN Genomic-tip 500/G was equilibrated with 10 ml QBT buffer. The clear lysate was applied to the column and allowed to pass through. Then the column was washed 2× with 15 ml QC buffer. Finally the genomic DNA was eluted with 5 ml QF buffer. The chromosomal DNA was then precipitated with isopropanol and transferred with a glass rod into TE buffer.

The amplified gene was cut with the restriction enzymes NdeI and HindIII and ligated into the multiple cloning site of the vector pDHE-vector, which possesses a rhamnose-inducible promoter. This vector was expressed in TG1 cells (DSMZ 6056).

This strain was fermented as fed-batch at 37° C. in a minimal medium. The cells were used in the tests as bio-moist-matter with a bio-dry-matter of 150 g/l. The specific enzyme activity was 50 U/g bio-dry-matter (BDM).

Example 2

Preparation of 3-amino-3-phenyl-propionic acid ethyl ester with a wild-type strain of *Rhodococcus equi*

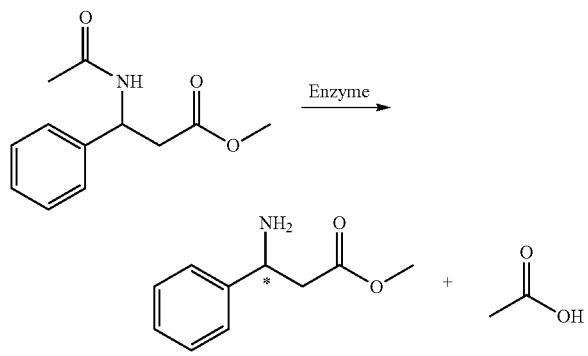

a) Preparation of the Cells:
Inoculate FP medium with cells. The cells are incubated at 28° C. and 180 rpm. After 20 h of growth, the wild type-strain is induced with a solution of 1 g/l 3-acetylamino-3-phenyl-propionic-acid ethyl ester and incubated for a further 7 h. The cells are lysed and the raw extract is used in the activity test.

b) Reaction of 3-acetylamino-3-phenyl-propionic acid ethyl ester:
In a buffer (100 mM $KH_2PO_4$ pH 7), 1 g/l 3-acetylamino-3-phenyl-propionic acid ethyl ester (AAPEE) and x µl (see Table 1) of cell-free raw extract (see Table 1) are incubated overnight at 28° C. or 40° C.

The formation of the amine or the degradation of the amide is measured by HPLC.

For determination of the enantioselectivity, the samples are measured by chiral GC.

Preparation:

TABLE 1

Preparations for the reaction of 3-acetylamino-3-phenyl-propionic acid ethyl ester

|  | 1 | 2 | 3 |
|---|---|---|---|
| Raw extract | 200 | 400 | 800 |
| 1M $KH_2PO_4$ pH 7 | 200 | 200 | 200 |
| $H_2O$ | 1380 | 1180 | 780 |
| Ester (100 g/l in acetone) | 20 | 20 | 20 |
| HCl | 200 | 200 | 200 |

Figure 2:
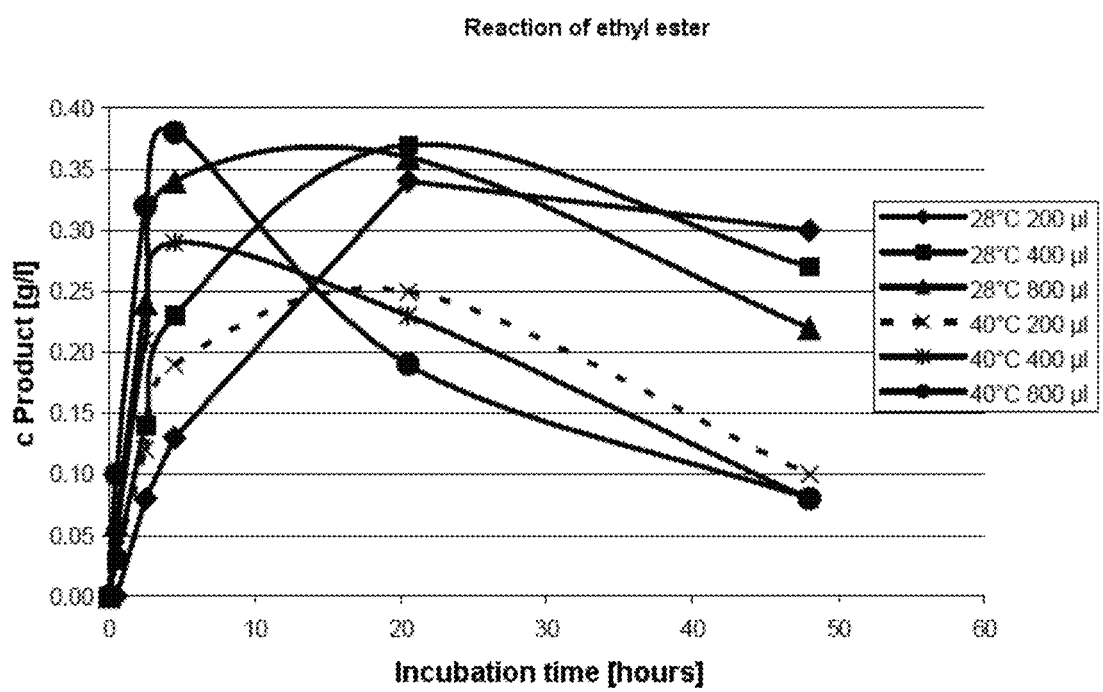
FIG. 2 shows formation of 3-amino-3-phenyl-propionic acid ethyl ester.

Results:
FIG. 1 shows the formation of 3-acetylamino-3-phenyl-propionic acid ethyl ester as a function of reaction time and temperature As can be seen from FIG. 2, the concentration of 3-amino-3-phenyl-propionic acid ethyl ester reaches a maximum after about 24 hours. After that, the amine that formed is also degraded. The reactions at 40° C. go faster at the beginning, but collapse earlier than at 28° C.

Analysis:
achiral HPLC
column: Onyx Monolith C18, 50*4.6 mm, from Phenomenex
Mob. Phase A: 20 mM $KH_2PO_4$ pH2.5
Mob. Phase B: Acetonitrile
Flow: 1.5 ml/min
Furnace temp.: 45° C.
Inj. vol.: 2 µl

| Gradient: | 0.0 min | 20% B |
|---|---|---|
|  | 0.5 min | 20% B |
|  | 0.6 min | 80% B |
|  | 1.2 min | 80% B |
|  | 1.3 min | 20% B |
|  | 2.0 min | 20% B |

Detection: UV 210 nm
Retention time Educt 1.49 min
Product 0.74 min
Chiral GC:
Solvent: Acetonitrile

| Derivatization | ~100 µl solution |
|---|---|
|  | +300 µl TFAA (trifluoroacetic acid anhydride) |
|  | leave to stand for ~30 minutes at 100° C. |
| GC conditions |  |
| Column | 25 m Lipodex G 0.25 mm internal 0.25 µm FD |
| Furnace program | 80/10/2/180/10/700 |
| Injection | 1-5 µl depending on concentration at 250° C. |

| Detector | FID at 250° C. |
|---|---|
| Carrier gas | Helium 16.7 PSI, flow 1.6 ml/min, split 100:1 |

Comparison: Reaction with racemic vs. enriched substrate
Test conditions: 500 mM AAPPEE (rac./enriched)
100 mM $KH_2PO_4$ pH 7.0
25 g/l (bio-dry-matter) cells from fermenter discharge (cloned enzyme from *Rhodococcus erythropolis*)
30° C.

Figure 3:
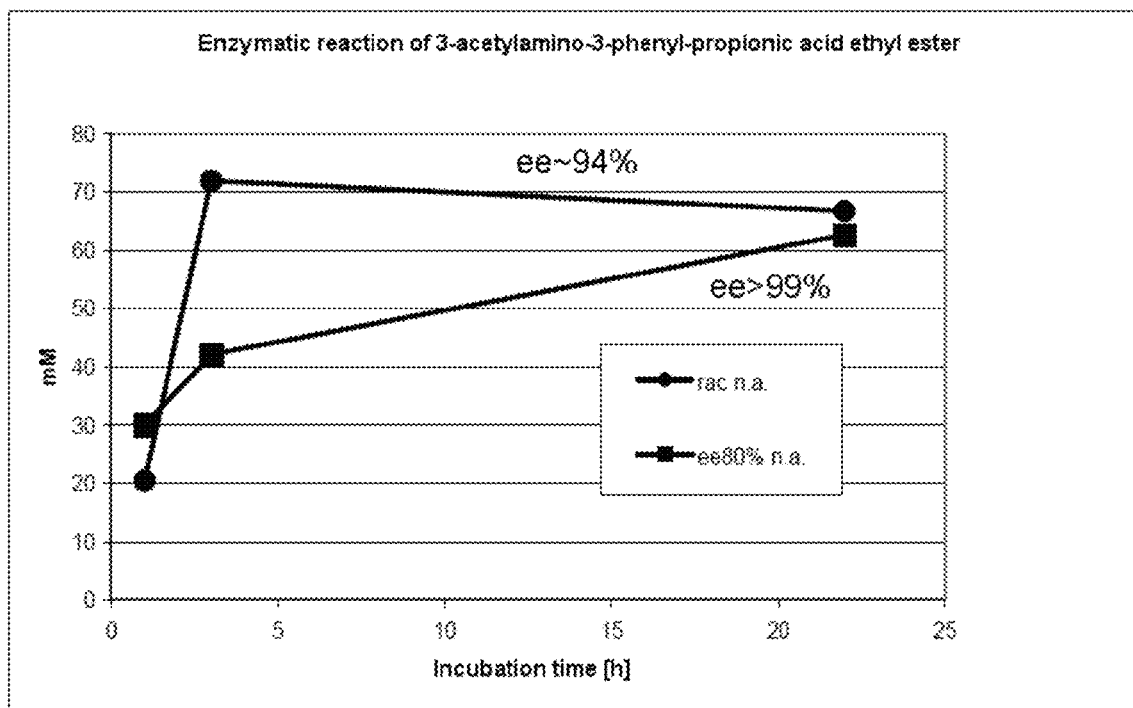
FIG. 3 shows a comparison of the reaction with racemic or enantiomer-enriched substrate.

FIG. 3 shows a comparison of the reaction with racemic or enantiomer-enriched substrate
Up to 20 g/l of 3-acetylamino-3-phenyl-propionic acid methyl ester (AAPEE) was reacted. If racemic substrate is used, enrichment of the S-enantiomer is obtained (ee~94%). However, if already enriched substrate is used (ee~80%), ee>99% can be achieved.
Preparative 4-l Preparation
4 l Preparation:
130 mM AAPPEE
100 mM $KH_2PO_4$ pH 7.0
34 g/L BDM cells (cloned enzyme from *Rhododcoccus erythropolis*)
30° C., 5 h
Preparation:

Set the reactor with 60 ml/102 g $H_3PO_4$ (85%) to pH 3.0. The final weight was 4113 g/4150 ml. The preparation was centrifuged (5000*g, 20 min) and the pellet was washed with 200 mL. A clear, slightly yellow supernatant was obtained (final weight 3804 g).

This was extracted with 3×1400 ml 2-butanol, first in order to separate educt and by-products from educt synthesis that are still present. Then, at 10° C., it was adjusted with 20% NaOH to pH 10 and the amino acid ester was isolated by extraction with 1500 ml 2-butanol and subsequent removal of the solvent under vacuum. 23.0 g of almost enantiomerically pure (99.3% ee) amino ester was obtained as slightly yellow oil. The chemical purity is >98% (GC).

Figure 4:
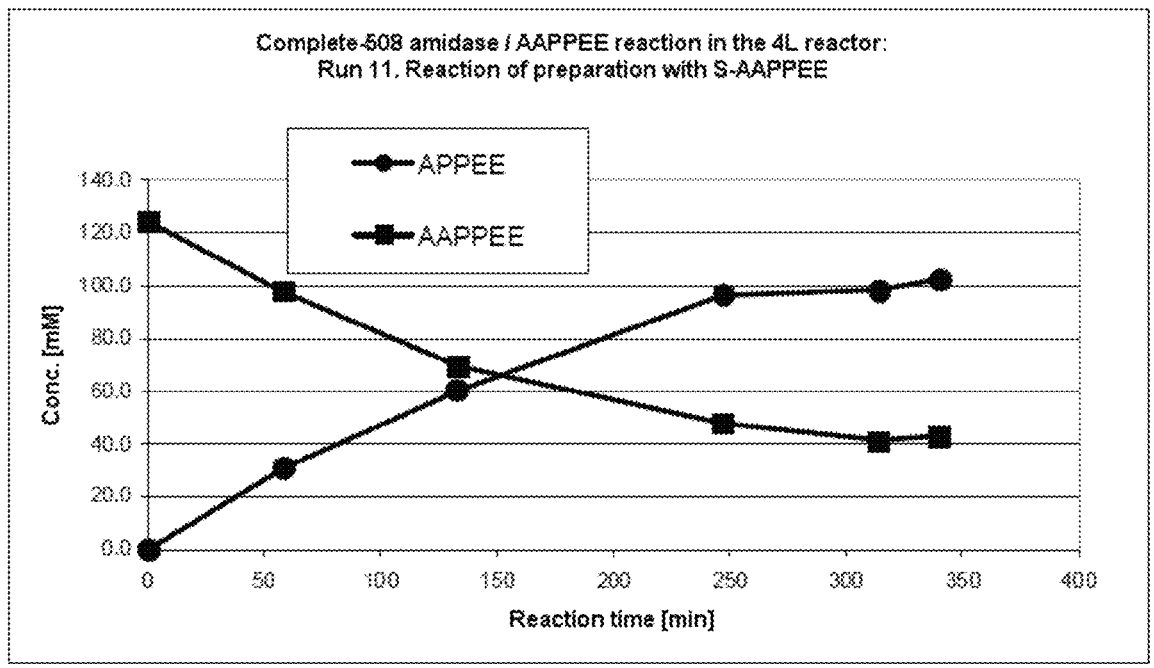
FIG. 4 shows the reaction of enriched S-AAPEE.
Figure 5:
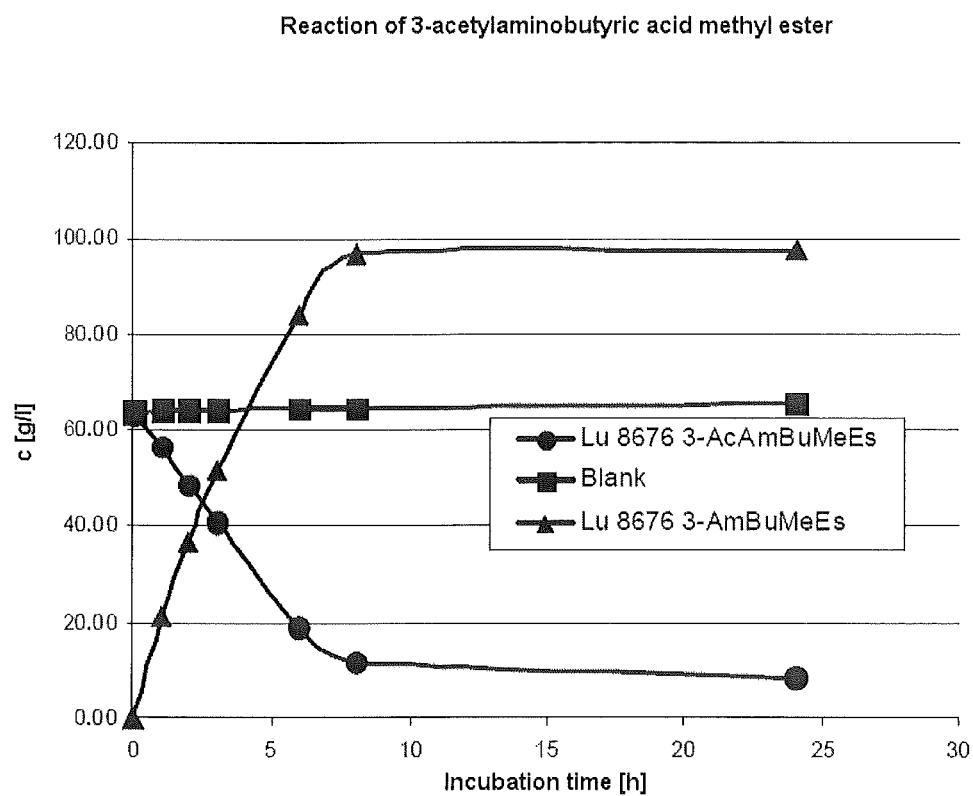
FIG. 5 shows variation of the concentrations of 3-acetylamino-butyric acid methyl ester (circles), 3-amino-butyric acid methyl ester (triangles), and a control without enzyme (squares). LU8676 denotes the *Rhodococcus erythropolis* wild-type strain.

FIG. 4 shows the reaction of enriched S-AAPEE

Example 3

Preparation of 3-aminobutyric acid methyl ester

The wild-type strain *Rhodococcus erythropolis* was used as amidase (SEQ ID NO:4). This amidase can be produced by genetic engineering methods that are familiar to a person skilled in the art, for example by expression of the nucleic acid according to SEQ ID NO:3 in a suitable host system, e.g. *E. coli*.

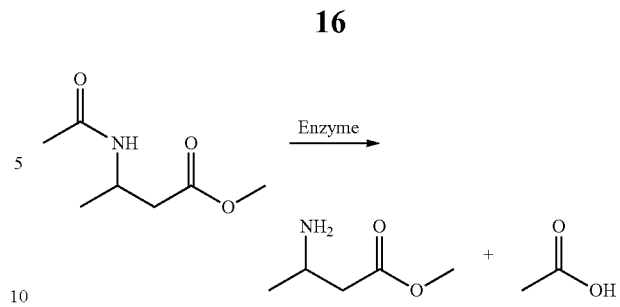

Execution similar to example 2.
Analysis:
achiral HPLC
Column: Luna C8(2), 150*3.0 mm, from Phenomenex
Mob. Phase A: 10 mM $KH_2PO_4$ pH2.5
Mob. Phase B: Acetonitrile
Flow: 1.0 ml/min
Furnace temp.: 40° C.
Inj. vol.: 1 µl

| Gradient: | 0.0 min | 0% B |
|---|---|---|
| | 7.0 min | 30% B |
| | 10 min | 30% B |
| | 1.2 min | 80% B |
| | 1.3 min | 20% B |
| | 2.0 min | 20% B |

Detection: UV 200 nm
Retention time Educt 4.35 min
Product 1.13 min
chiral GC
Column: Hydrodex-β-6-TBDM, 25*0.25 mm, film thickness 16 µm M&N
Temp. progr.: 90° C., 15 min, 10° C., 10 min, 160° C., 15 min
Detector: FID
Retention time Educt enant. 1 21.46 min
(educt only)
Preparation:

TABLE 2

Preparations for the reaction of 3-acetylamino-butyric acid methyl ester

| | 60 g/l | Blank |
|---|---|---|
| Enzyme | 1000 µl | 0 µl |
| 1M $KH_2PO_4$ pH 7 | 200 µl | 200 µl |
| Substrate | 200 µl | 200 µl |
| | (pure substrate) | (pure substrate) |
| VE-$H_2O$ | 400 µl | 1400 µl |
| HCl | 200 µl | 200 µl |

FIG. 6 shows the variation of the concentrations of 3-acetylamino-butyric acid methyl ester, 3-amino-butyric acid methyl ester, and a control without enzyme, LU8676 denotes the *Rhodococcus erythropolis* wild-type strain.

The invention claimed is:

1. A process for producing optically active 3-aminocarboxylic acid ester compounds of general Formula I, and the ammonium salts thereof,

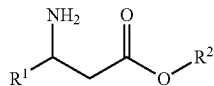
(I)

wherein

R¹ stands for alkyl, alkoxyalkyl, alkenyl, cycloalkyl, heterocycloalkyl, aryl, or hetaryl, and R² stands for alkyl, cycloalkyl or aryl, in which an enantiomeric mixture of a simply N-acylated 3-aminocarboxylic acid ester of general formula (I.b),

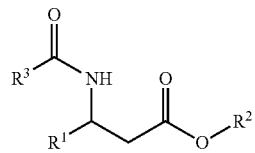
(I.b)

in which R¹ and R² have the meanings given above and R³ stands for hydrogen, alkyl, cycloalkyl or aryl, is submitted to an enantioselective deacylation by adding a polypeptide with amidase activity selected from the group consisting of:
   a) a polypeptide comprising the amino acid sequence according to SEQ ID NO: 2; and
   b) a polypeptide comprising an amino acid sequence that has at least 96% sequence identity with SEQ ID NO: 2.

2. A process for producing optically active 3-aminocarboxylic acid ester compounds of general Formula I', and derivatives thereof,

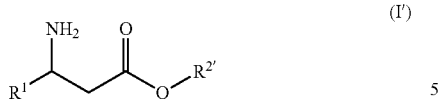

(I')

in which
R¹ stands for alkyl, alkoxyalkyl, alkenyl, cycloalkyl, heterocycloalkyl, aryl, or hetaryl, and
R² stands for hydrogen, a cation equivalent M+, alkyl, cycloalkyl or aryl, in which
a) a β-ketoester of general Formula I.1

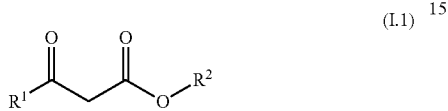

(I.1)

in which R¹ and R² have the meanings given above, is reacted
a 1) with at least one carboxylic acid amide of formula R³—C(O)NH₂, in which R³ has the meaning given above, in the presence of an amidation catalyst, or
a 2) with ammonia and then with a carboxylic acid derivative of formula R³—C(O)X, in which X stands for halogen or a residue of formula OC(O)R⁴, in which R⁴ has the meaning given above for R³,
obtaining the corresponding N-acylated, α-β-unsaturated (Z)-3-aminocarboxylic acid ester, of general formula (I.a),

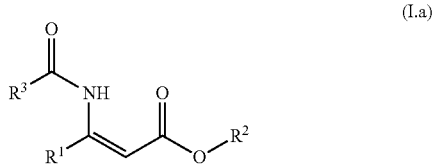

(I.a)

in which R¹, R² and R³ have the meanings given above, b) the enamide (I.a) obtained in this reaction is submitted to a hydrogenation, obtaining an enantiomeric mixture of simply N-acylated β-aminocarboxylic acid esters of general formula (I.b),

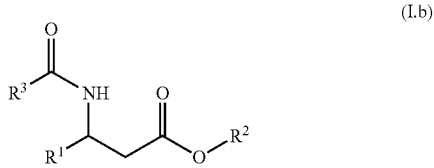

(I.b)

in which R¹, R² and R³ have the meanings given above,
c) the enantiomeric mixture of compounds I.b obtained in the hydrogenation is submitted to an enantioselective deacylation by adding a polypeptide as defined in claim 1 and the resultant ammonium salt of a 3-aminocarboxylic acid ester, enriched with respect to a stereoisomer, is isolated, and
d) optionally the ammonium salt isolated is converted to the 3-aminocarboxylic acid ester, and
e) optionally the 3-aminocarboxylic acid ester is converted to the free 3-aminocarboxylic acid or a salt thereof.

3. The process according to claim 1, wherein a β-ketoester of Formula I.1 is reacted with at least one carboxylic acid amide of formula R³—C(O)NH₂, in the presence of an amidation catalyst, with removal of the reaction water, to a 3-aminocarboxylic acid ester of Formula I.a.

4. The process according to claim 1, wherein the deacylation is carried out in aqueous buffer as reaction medium.

5. The process according to claim 2, wherein the hydrogenation b) is carried out in the presence of a hydrogenation catalyst, which comprises at least one complex of a transition metal of groups 8 to 11 of the periodic table of the elements and comprises, as ligand, at least one chiral, phosphorus atom-containing compound.

6. The process according to claim 1, wherein R¹ stands for phenyl and R² and R³ have the meanings stated in claim 1.

* * * * *